United States Patent [19]

Renga et al.

[11] Patent Number: 4,595,763

[45] Date of Patent: * Jun. 17, 1986

[54] PROCESS FOR PREPARING METHYL ETHERS OR THIOETHERS OF ARYL COMPOUNDS

[75] Inventors: James M. Renga; Pen-Chung Wang, both of Midland, Mich.

[73] Assignee: The Dow Chemical Company, Midland, Mich.

[*] Notice: The portion of the term of this patent subsequent to Sep. 14, 1999 has been disclaimed.

[21] Appl. No.: 507,910

[22] Filed: Jun. 27, 1983

Related U.S. Application Data

[63] Continuation of Ser. No. 284,035, Jul. 17, 1981, abandoned.

[51] Int. Cl.⁴ ............... C07C 41/01; C07C 41/12; C07C 43/02; C07C 79/35

[52] U.S. Cl. .................... 546/290; 546/288; 546/296; 546/297; 546/303; 568/584; 568/585; 568/586; 568/587; 568/588; 568/630; 568/631; 568/632; 568/633; 568/634; 568/649; 568/655; 558/423

[58] Field of Search .............. 568/588, 649, 655, 584, 568/585, 586, 587, 630, 631, 632, 633, 634; 260/465 F, 465 H; 546/290, 296, 287, 297, 288, 303

[56] References Cited

U.S. PATENT DOCUMENTS 4,349,487 9/1982 Renga et al. .................... 260/465 F

OTHER PUBLICATIONS

Eastman Organic Chemical Bulletin, vol. 48, No. 1, (1976).

Weber et al., Phase Transfer Catalysis in Organic Synthesis, pp. 73–84, Springer-Verlag, Berlin, Heidelberg & N.Y. (1977).

*Primary Examiner*—Alan L. Rotman

[57] ABSTRACT

Aromatic hydroxyl- or thiol-containing compounds are methylated by contacting with methyl trichloroacetate at elevated temperatures in the presence of an initiator.

6 Claims, No Drawings

PROCESS FOR PREPARING METHYL ETHERS OR THIOETHERS OF ARYL COMPOUNDS

CROSS-REFERENCE TO RELATED APPLICATION

This is a continuation of application Ser. No. 284,035 filed July 17, 1981, now abandoned.

BACKGROUND OF THE INVENTION

This invention relates to a new chemical process, more particularly to a new method for methylating aromatic hydroxyl- or thiol-containing compounds. The resulting products obtained by the instant process have various uses as chemical intermediates, as heat transfer media, as herbicides and in other industrial applications.

In the past, aromatic ethers have been produced by alkylation of the phenoxide ion usually generated by treatment of a phenolic compound with a base such as sodium hydroxide followed by treatment with an alkyl halide, sulfate or sulfonate. The process is disfavored for commercial use because of the formation of metal salt by-products.

Alternate processes which do not form unacceptable by-products are also known. Direct alkylation of phenols by treatment with diazomethane, tetramethoxymethane or pentamethoxyphosphorane, have been previously disclosed in the art. Other processes involve treating phenol with methanol in the presence of dicyclohexylcarbodiimide or a mixture of diethylazodicarboxylate and triphenylphosphine. These processes have proven to be rather inefficient, uneconomical or ecologically unsuitable.

A suitable methylating process which avoids the disadvantages of prior art methods is desired.

SUMMARY OF THE INVENTION

It has now been found that aromatic hydroxyl or thiol-containing compounds of the formula Ar(XH)$_n$ may be readily methylated by reaction with methyltrichloroacetate in the presence of a catalytic amount of an initiator.

DETAILED DESCRIPTION OF THE INVENTION

The phenols or thiophenols for use in the invented process are compounds of formula Ar(XH)$_n$, where X is oxygen or sulfur, Ar is any aromatic carbocyclic or nitrogen- and carbon-containing heterocyclic group, unsubstituted or substituted with one or more groups unreactive under the reaction conditions and n is an integer from 1 to about 3 which represents the valence of Ar.

In the above formula, a monovalent Ar can be phenyl, naphthyl, biphenylyl, pyridyl, furyl, quinolyl, benzofuryl, pyridazyl, indolyl, benzothiazolyl, or the like, unsubstituted or substituted with up to three unreactive groups. Such unreactive groups may be either electron-donating or electron-withdrawing substituents and include lower alkyl, lower alkoxy, halo, cyano, nitro, ester groups, trifluoromethyl, aralkyl and phenoxy. If n is greater than one, Ar represents the divalent or trivalent equivalents of the above, e.g., phenylene, naphthylylene, alkylidene diphenylene, alkylene triphenylene, oxydiphenylene, pyridylene, etc., also substituted or unsubstituted as described.

Preferably the aromatic hydroxyl- or thiol-containing compound is phenol or an inertly-substituted phenol.

In the invented process, the hydroxyl- or thiol-containing aromatic compound is contacted with methyltrichloroacetate in a suitable reactor vessel. Generally, reactors of ordinary design and construction may be employed. The reactants are combined in any order and reacted at an elevated temperature from about 100° C. to about 180° C. Preferred temperatures are from about 110° C. to about 150° C. Generally, the reaction is conducted under atmospheric pressure although elevated or reduced pressures may also be employed if so desired.

The reactants may be combined in any ratio, however, when an excess of methyl trichloroacetate is employed, high yields of the resulting ether are observed. Preferred molar ratios of hydroxyl- or thiol-containing aromatic compound to methyltrichloroacetate are from about 1:1 to 1:2.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and alkoxides. Additional suitable initiators include stable quaternary salts such as ammonium or phosphonium quaternary salts having inert counterions. Preferably, these salts have the general formula (R")$_4$AY where each R" is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The R" groups may be alkyl, aryl, alkaryl, aralkyl, or cycloalkyl. Also, two R" groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

It is believed the various initiator compounds operate according to different mechanisms. For example, basic catalysts are believed to react with the aromatic hydroxyl- or thiol-containing reactant, deprotonating the reactant and thereby producing a species capable of demethylating methyl trichloroacetate. Quaternary salts on the other hand, appear to activate methyl trichloroacetate directly providing an active species able to react with the aromatic compound.

The quantity of initiator compound is not critical so long as any significant amount is present and available at the reaction site. Suitably from about 0.01–1 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts include the compounds generally known as phase-transfer catalysts such as, for example, cyclic oligomers of ethylene oxide known as crown ethers. Such solubilizing agents may be employed in minor amounts, for example, in the ratio of about 0.005–1.0 mole per mole of basic catalyst.

A reaction solvent is usually not required or desirable, but use of a solvent may be advantageous under some conditions, e.g., when low boiling reactants or solid reaction products are involved. Excess methyltrichloroacetate can be used as the solvent if desired. Polar solvents appear to increase the rate of reaction. Relatively high boiling inert solvents such as N,N-dimethylformamide, sulfolane, dimethylsulfoxide, glycol diethers, and substituted aromatics such as anisole, o-dichlorobenzene, alkylated pyridines, and the like are suitable.

In the usual operation of the process the reactants and initiator are combined in a reactor as previously described. Suitably the reactor is provided with a distillation head or other means to remove the volatile reaction by-products, chloroform and carbon dioxide formed during the course of the reaction. The by-products distill off substantially as formed and provide a useful indication of the course of the reaction. Because the by-products may themselves be commercially valuable, they may be collected as condensate in a suitable receiver. A stream of nitrogen or other inert purging gas may be employed to aid in removing volatile reaction products.

The reaction proceeds rapidly and generally is completed in from about 1 to about 5 hours depending of course on the amounts of reactants, temperature and other reaction conditions. The product is the corresponding methyl ether or thioether of the original hydroxyl- or thiol-substituted aromatic compound, excepting however, that 2- or 4-hydroxy-substituted pyridines methylate the nitrogen of the ring as is previously known, thereby forming the corresponding pyridinone, e.g., compounds of the formula

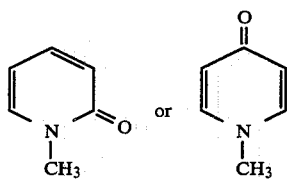

Tne products are recovered from the reaction vessel and separated from residual catalyst if desired by ordinary techniques such as distillation.

SPECIFIC EMBODIMENTS

Having described the invention, the following examples are provided as further illustrative and are not to be construed as limiting the invention.

EXAMPLE 1

In a 25 ml round-bottom flask equipped with a distillation head, a mixture of phenol (2.35 g, 0.025 mole), methyl trichloroacetate (5.32 g, 0.03 mole), potassium carbonate (0.069 g, 0.0005 mole) and 18-crown-6 cyclic polyether (0.132 g, 0.0005 mole) was heated to 150° C. with stirring. Gas evolution was observed between about 100° C. and 150° C. The reaction was continued for about 2 hours. The product was isolated by distillation and analyzed by nuclear magnetic resonance spectroscopy and found to be methoxy benzene. Purified yield was 96 percent.

EXAMPLES 2–10

The reaction conditions of Example 1 were substantially repeated to prepare the methylated reaction products of Table I in the indicated yields.

TABLE I

| Reactant | Ether | % Yield |
|---|---|---|
| o-chlorophenol | o-chloromethoxybenzene | 85 |
| p-methoxyphenol | p-dimethoxybenzene | 88 |
| p-chlorophenol | p-chloromethoxybenzene | 90 |
| 2,4-dichlorophenol | 2,4-dichloromethoxybenzene | 80 |
| p-nitrophenol | p-nitromethoxybenzene | 88 |
| p-cyanophenol | p-cyanomethoxybenzene | 92 |
| 2-hydroxy pyridine | N—methyl-2-pyridone | 80 |
| 6-methyl-2-hydroxy pyridine | N—methyl-6-methyl-2-pyridone | 75 |
| 5-chloro-2-hydroxy pyridine | N—methyl-5-chloro-2-pyridone | 74 |
| 2-pyridine thiol | 2-(methylmercapto)pyridine | 96 |

EXAMPLES 11–13

The reaction conditions of Example 1 were substantially repeated excepting that each of the initiators identified in Table II was substituted in place of potassium carbonate. Additionally, no crown ether was used. The percent conversion of phenol to anisole after the indicated time periods was calculated from data obtained by nuclear magnetic resonance spectoscopy.

TABLE II

| Catalyst | Time (hr) | % Conversion |
|---|---|---|
| 4-(dimethylamino)pyridine | 12 | 58 |
| tetra-n-butylammonium bromide | 4 | 75 |
| tetra-n-butylphosphonium bromide | 4 | 80 |

EXAMPLE 14

The reaction conditions of Example 1 were substantially repeated excepting that a solvent was employed. Accordingly, 4-hydroxypyridine (1.2 g, 0.0125 mole), methyl trichloroacetate (2.66 g, 0.015 mole), potassium carbonate (0.035 g) and 18-crown-6 cyclic polyether were combined in 5 ml of N,N-dimethylformamide in a 25 ml round-botton flask fitted with a distillation head. The mixture was warmed with stirring to 150° C. Gas evolution was observed to begin at about 80° C. After heating for 3 hours, the contents remaining in the flask were collected. After solvent removal the product, 1-methyl-4-pyridone, was purified by Kugelrohr distillation at 200° C.–220° C./1 mm and identified by nuclear magnetic resonance spectroscopy. Yield was 0.95 g (70 percent) of a colorless liquid.

What is claimed is:

1. A process for preparing methyl aryl ethers or thioethers corresponding to the formula:

ArXCH$_3$ wherein:
when X is oxygen, Ar is phenyl, naphthyl or biphenyl, optionally substituted with up to three unreactive moieties selected from the group consisting of lower alkyl, lower alkoxy, halo, cyano, nitro, trifluoromethyl, aralkyl, and phenoxy provided that at most only two such moieties are cyano, nitro or aralkyl moieties; and when X is sulfur, Ar is phenyl, naphthyl, biphenyl or pyridyl, optionally substituted with up to three unreactive moieties selected from the group consisting of lower alkyl, lower alkoxy, halo, cyano, nitro, trifluoromethyl, aralkyl and phenoxy provided that at most only two such moieties are cyano, nitro or aralkyl moieties, comprising contacting an aromatic hydroxyl- or thiol-containing compound of the formula ArXH, where Ar and X are as previously defined, with methyl trichloroacetate in the presence of a catalytic amount of an initiator selected from the group consisting of phosphonium salts, alkali metal alkoxides, salts of a strong base and a weak acid, aliphatic tertiary amines and aromatic tertiary amines at a temperature from about 100° C. to 180° C.

2. The process according to claim 1 wherein the initiator comprises a basic catalyst and a solubilizing agent.

3. The process according to claim 2 wherein the basic catalyst is an alkali metal carbonate and the solubilizing agent is a cyclic polyether.

4. The process according to claim 1 wherein the temperature of the reaction is from about 110° C. to about 150° C.

5. The process according to claim 1 wherein the aromatic hydroxyl- or thiol-containing compound is phenol or lower alkyl- lower alkoxy-, halo-, cyano-, nitro-, trifluoromethyl-, aralkyl-, or phenoxy-substituted phenol.

6. The process according to claim 1 wherein the basic catalyst is selected from the group consisting of the alkali metal alkoxides, salts of strong bases and weak acids, and non-nucleophilic organic bases.

* * * * *